United States Patent [19]

Meyer et al.

[11] Patent Number: 4,939,336

[45] Date of Patent: Jul. 3, 1990

[54] METHOD AND APPARATUS FOR MATERIAL PROCESSING WITH THE AID OF A LASER

[75] Inventors: Wilhelm Meyer; Ralf Engelhardt, both of Lübeck, Fed. Rep. of Germany

[73] Assignee: Telemit Electronic GmbH, Fed. Rep. of Germany

[21] Appl. No.: 253,064

[22] Filed: Oct. 3, 1988

[30] Foreign Application Priority Data

Oct. 3, 1987 [DE] Fed. Rep. of Germany ....... 3733489

[51] Int. Cl.[5] ............................................. B23K 26/00
[52] U.S. Cl. ........................... 219/121.62; 219/121.83; 606/7
[58] Field of Search ...................... 219/121.62, 121.61, 219/121.83, 121.6, 121.85; 128/303.1

[56] References Cited

U.S. PATENT DOCUMENTS

| | | | |
|---|---|---|---|
| 4,443,684 | 4/1984 | Sakuragi et al. | 219/121.69 |
| 4,504,727 | 3/1985 | Melcher et al. | 219/121.62 |
| 4,682,594 | 7/1987 | Mok | 128/303.1 |
| 4,720,621 | 1/1988 | Langen | 219/121.68 X |

FOREIGN PATENT DOCUMENTS

| | | |
|---|---|---|
| 0195375 | 9/1986 | European Pat. Off. . |
| 2647618 | 4/1978 | Fed. Rep. of Germany . |
| 3245846 | 7/1983 | Fed. Rep. of Germany . |
| 3507299 | 9/1985 | Fed. Rep. of Germany . |
| 454302 | 6/1968 | Switzerland . |

OTHER PUBLICATIONS

Teng et al., Optical Studies of Pulsed-Laser ..., Appl. Phys. B, 42 (1987), pp. 73–78.

Primary Examiner—C. L. Albritton
Attorney, Agent, or Firm—Ostrolenk, Faber, Gerb & Soffen

[57] ABSTRACT

In a method and an apparatus for material processing with the aid of a laser the laser light is directed via a laser optical system onto the material and the light reemitted or scattered back by the material is conducted via the laser optical system onto a detector arrangement which is followed by an evaluating circuit for controlling the laser. The amplitude-versus-time profile of the light incident on the detector arrangement is evaluated and used to control the laser and/or an optical switch arranged in the output beam path of the laser.

19 Claims, 5 Drawing Sheets

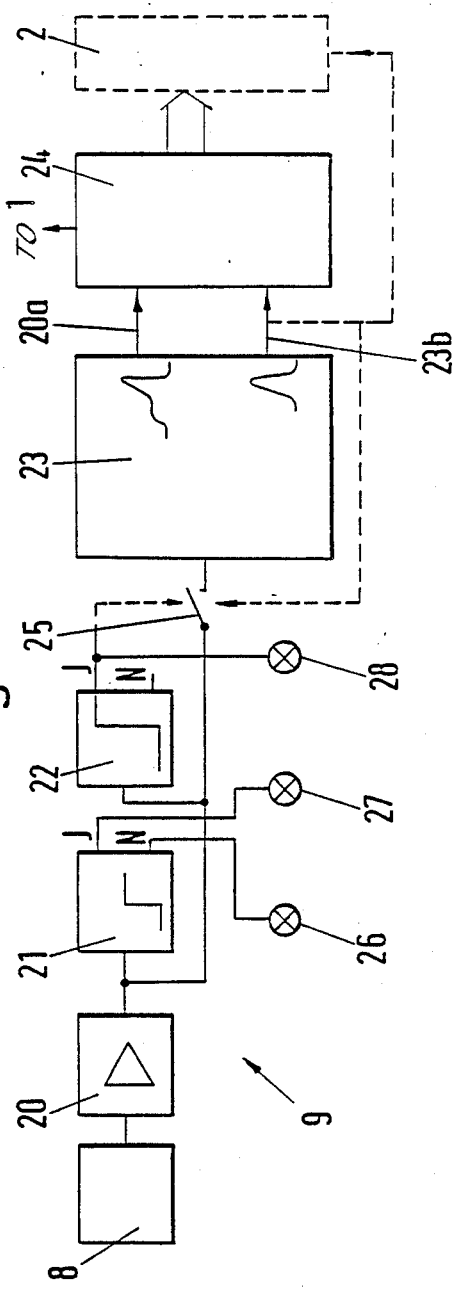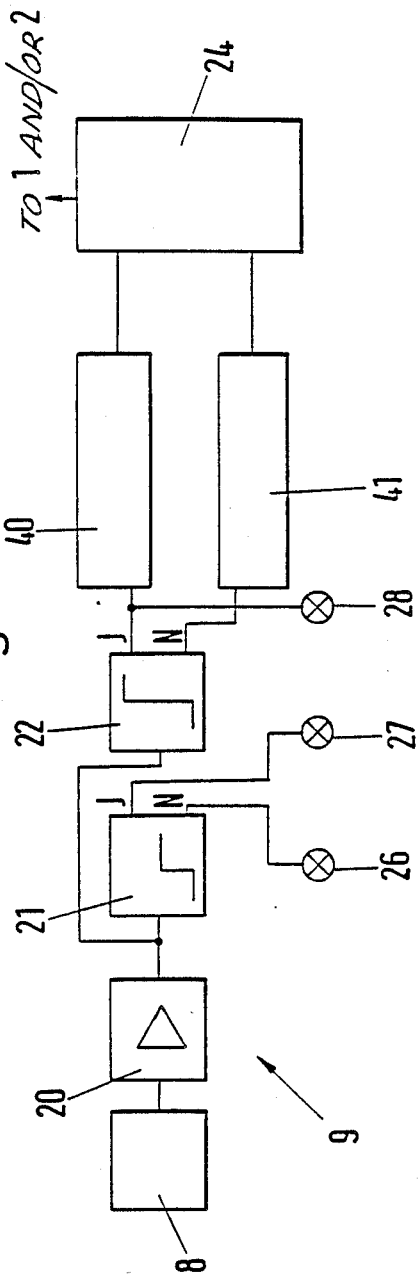

METHOD AND APPARATUS FOR MATERIAL PROCESSING WITH THE AID OF A LASER

BACKGROUND AND SUMMARY OF THE INVENTION

The invention relates to a method and an apparatus for material working or processing with the aid of a laser, and more particularly to such method and apparatus in which the laser light is directed via a laser optical system onto the material and the light reemitted or scattered back by the material is conducted via the laser optical system to a detector arrangement which is followed by an evaluating circuit for controlling the laser.

In a known method of this type (Optical Studies of Pulsed Laser Fragmentation of Biliary Calculi, Applied Physics B, Springer Publications 1987 pages 73–78) the output signal of a laser is directed via a laser optical system and an optical wave guide onto urinary and biliary calculi to fragment the latter. In the laser optical system a semireflecting mirror is disposed which conducts a part of the light reemitted, reflected back or scattered back by the stone, which is returned via the optical waveguide, onto a detector 1 which is followed by an evaluating circuit in the form of a spectral analyzer.

It is very difficult here to lead the optical waveguide in such a manner that a detrimental effect on the tissue surrounding the stone is completely excluded. A visual control or a control with the aid of radiological methods also cannot exclude with certainty that the laser energy strikes tissue parts.

The invention is based on the problem of providing a method and an apparatus of the type mentioned at the beginning in which with low expenditure limitation of the working or processing to the desired regions or materials is automatically achieved so that for example in the case of fragmentation of human stones, such as urinary and biliary calculi, damage to the tissue embedding the stone is avoided with certainty.

This problem is solved by having the amplitude-versus-time profile of the light incident on the detector arrangement evaluated after passage of a predetermined period of time from the start of the laser light, and used for controlling the laser and/or an optical switch arranged in the output beam path of the laser characterizing clause of claim 1 or 11. Advantageous embodiments and further developments of the invention are set forth in the respective subsidiary claims.

With the configuration of the method and apparatus according to the invention exactly controllable working of the material to be processed is achieved, as is essential in particular when using the method and apparatus for fragmenting human stones, for example urinary and biliary calculi. The laser may be controlled in such a manner that pulse emission which preserves the tissue, i.e. is stone-selective, is obtained. The regulation of the energy applied may be effected via changing the power density or changing the pulse duration or controlling both these parameters.

According to a further embodiment the laser pulse is interrupted before reaching its maximum energy when the output signal of the detector arrangement within a predetermined time after triggering the laser pulse does not exceed a predetermined threshold value. In this embodiment the detection according to the invention takes account of the fact that the output signal of the detector arrangement, when the laser pulse strikes hard material, assumes considerable values only a short time after triggering of the laser pulse whilst a rise of said output signal does not take place until after a considerably longer time when the pulse meets tissue material or soft material. If therefore within a predetermined time after triggering of the laser pulse a rise of the output signal has not yet taken place this means that the laser pulse is striking relatively soft material and can then be terminated before reaching its maximum value for example by closing an optical switch.

The method and apparatus according to the invention are also suitable for working other materials, for example narrowly defined regions of semiconductor materials in the fabrication of integrated circuits.

A further use is for example in angioplasty.

In the method and apparatus according to the invention the laser and the optical switch following said laser are controlled in accordance with one embodiment so that firstly only measuring pulses are emitted, their pulse energy being kept so low that no dielectric breakdown yet occurs. The time function profile of the light incident on the detector arrangement is evaluated. If this evaluation shows the presence of material to be processed or worked the laser energy is increased to ensure that the dielectric breakdown occurs only at the material to be worked, for example the stone.

Subsequently, it is then possible with each working pulse to make an analysis of the amplitude-versus-time profile of the light incident on the detector, said time function course or profile changing clearly when the laser pulse strikes surrounding material instead of the material to be worked. When this is detected the laser energy is reduced to a lower value.

It is alternatively possible to cause a measuring pulse to follow each working pulse of high energy, said measuring pulse determining whether material still to be processed is struck by the laser pulse. In each case damage to the material surrounding the material to be worked can be avoided with certainty.

Furthermore, according to a preferred embodiment it is possible with the aid of an optical switch to interrupt a laser pulse before the maximum energy is reached when the time profile of the output signal of the detector arrangement indicates that the laser pulse is not directed onto material to be worked so that damage to material which is not to be worked is avoided.

In addition to the optical evaluation the acoustic signal accompanying the dielectric breakdown can be detected and evaluated for example to determine the number of working impulses applied for documentation purposes.

BRIEF DESCRIPTION OF THE DRAWINGS

The invention will be explained in detail hereinafter with reference to examples of embodiment illustrated in the drawings, wherein:

FIG. 8 shows a first embodiment of the evaluating circuit, FIG. 9 shows a second embodiment of the evaluating circuit.

DETAILED DESCRIPTION OF THE PREFERRED EMBODIMENTS

Figure 1:
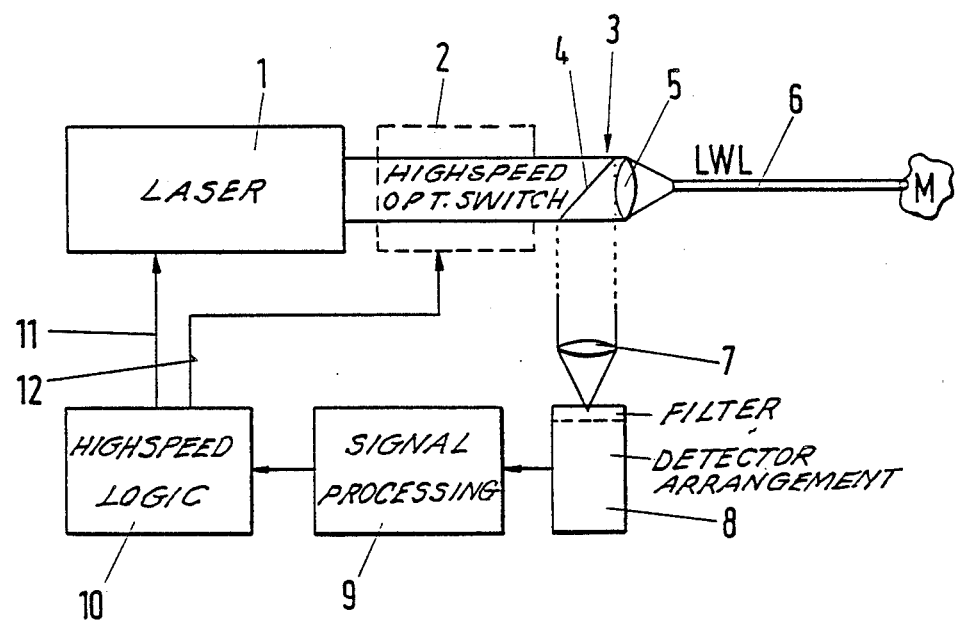
FIG. 1 shows an embodiment of an apparatus for carrying out the method.

The embodiment of an apparatus shown in FIG. 1 comprises a laser 1 of which the output pulses are supplied via an optical switch 2 having a high switching speed to a laser optical system of which the output is directed via an optical fibre or waveguide 6 to the material M to be processed or worked. In the embodiment illustrated the laser optical system 3 comprises for example a semireflecting mirror 4 and a first lens 5 for focusing the laser light pulse onto the optical waveguide 6. Light reemitted, scattered back or reflected back by the material M to be worked passes via the optical waveguide 6, the lens 5 and the semireflecting mirror 4 to a further lens 7 which focuses this light on a detector arrangement. The output signal is supplied to an evaluating circuit which will be described in further detail with the aid of FIGS. 8 and 9 and which via logic circuits 10 controls the optical switch 2 via an output line 12. As indicated by a further output line 11 of the logic circuit 12 the latter can also control the laser 1 itself and the optical switch 2 possibly omitted.

When a laser pulse of high energy strikes the material M to be processed in the immediate vicinity of this material to be worked a dielectric breakdown is produced which initiates a shock wave for working the material.

This material may for example be a human stone, for example a urinary or biliary calculus, which is embedded in surrounding tissue. In this case the shock wave effects a stone fragmentation. The resulting plasma bubble effects due to the high temperature of the plasma and the resulting pressure wave a splitting off, carrying away or fragmentation at the target area. It must however be ensured in many cases, in particular in the case considered of human stones, that the laser pulse emerging at the end of the optical wave guide 6 strikes only the material M to be worked and not the surrounding tissue, to prevent destruction of the latter.

The detector arrangement 8 permits in conjunction with the evaluating circuit 9 a very rapid determination whether material to be worked is arranged at the end of the optic waveguide 6 or whether said end of the waveguide is directed onto material which must not be subjected to the laser pulse, at least not to a laser pulse of full power.

For this purpose the evaluating circuit evaluates the amplitude-versus-time function variation of the light instant on the detector arrangement, this evaluation being based on fundamental ideas which will be explained in detail hereinafter with the aid of the diagrams according to FIGS. 2-6.

In the upper part of each of the diagrams the laser pulse itself is represented whilst in the lower part the output signal of the detector arrangement is represented, the abscissae representing the time variation and the ordinates the amplitude of the respective pulses.

Figure 2:
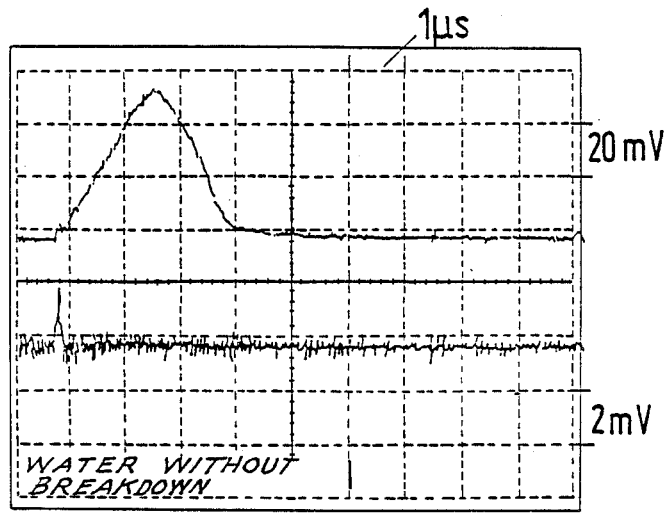
FIGS. 2–6 are diagrams showing examples of the time function path or profile of the light incident on the detector arrangement.
Figure 3:
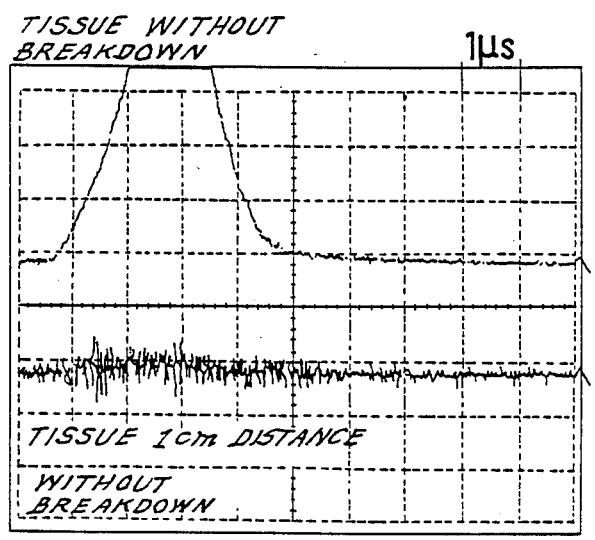
Figure 4:
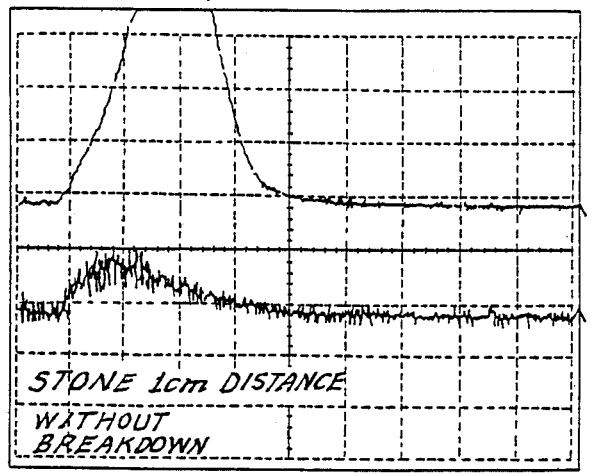

FIGS. 2-4 show the case where laser pulses of low power are emitted, subsequently referred to as measuring pulses.

FIG. 2 shows the case in which the end of the optical waveguide 6 is directed onto water. It can be seen that in this case only output signals of the detector arrangement occur which lie almost in the noise range.

FIG. 3 shows the case in which the end of the optical waveguide 6 is arranged at a distance of one centimeter from human tissue material. In this case it can be seen that the output signal of the detector arrangement 8 attains substantially greater amplitudes than in the case of FIG. 2.

Finally, FIG. 4 shows the case in which the end of the optical waveguide is arranged at a distance of one centimeter in front of the human stone to be processed and to be fragmented. It is clearly apparent from a comparison of FIGS. 2-4 that on emission of the measuring pulse on approaching a stone a substantially higher amplitude of the output signal of the detector arrangement occurs which can be used to detect the fact that the end of the optical waveguide is arranged adjacent to said stone.

Figure 5:
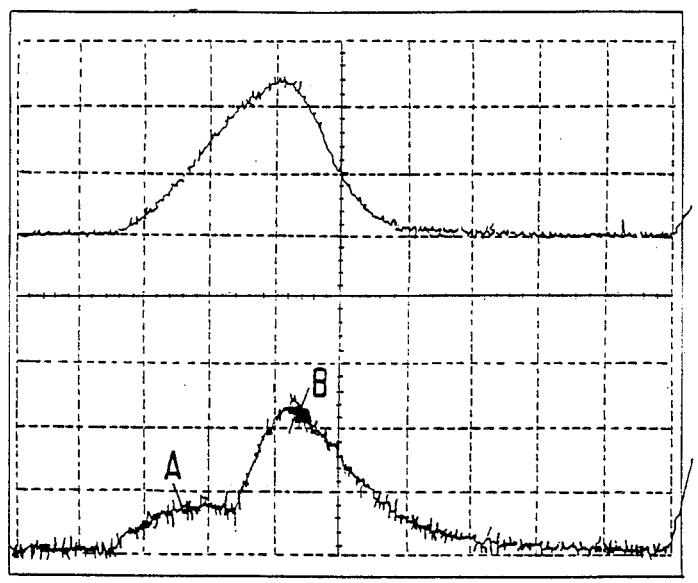
Figure 6:
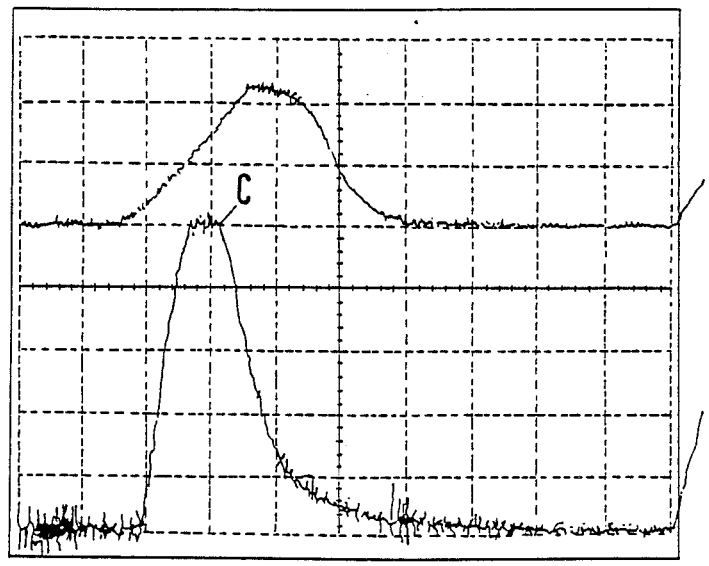

These conditions are reversed to a certain extent on emission of a working pulse as can be seen from FIGS. 5 and 6. FIG. 5 shows the case in which the energy of the laser pulse is so high that an electrical breakdown occurs at the end of the optical waveguide 6. In this case when the laser pulse strikes the stone firstly a relatively gradual rise A according to FIG. 5 occurs and this is followed by a higher pulse tip at the output of the detector arrangement 8. If however the breakdown occurs in the tissue material a single relatively high pulse tip C in accordance with FIG. 6 immediately occurs.

Figures 7A, 7B:
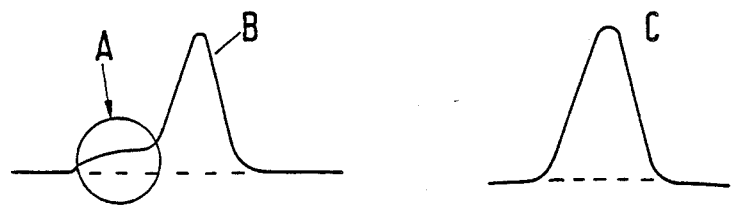
FIGS. 7A and 7B show idealized illustrations of the curve profiles of FIGS. 5 and 6.

FIGS. 7a and 7b, show this light amplitude-versus-time profile in idealized form, FIG. 7a corresponding to FIG. 5 and FIG. 7b, corresponding to FIG. 6. It can be seen that on dielectric breakdown at a stone according to FIG. 7a there is again firstly a relatively shallow rise A of the output signal of the detector arrangement which is followed by a pronounced pulse tip B. On occurrence of a dielectric breakdown in tissue in accordance with FIG. 7b only a pulse tip C occurs on its own.

On the basis of this knowledge of the amplitude-versus-time profile of the light incident on the detector arrangement according to FIG. 1 it is possible to construct with low expenditure evaluating circuits which permit a clear detection whether the end of the optical waveguide is directed onto a material surrounding the material to be worked or onto the material to be worked itself.

Examples of embodiment of such evaluating circuits are illustrated in FIGS. 8 and 9.

Common to both embodiments is that the detector arrangement 8 is followed by a signal amplifier 20 of which the output signal is supplied to the inputs of a first threshold value detector 21 and a second threshold value detector 22.

Common to both threshold value detectors is that they have two outputs which are denoted by J and N. At the output J of the threshold value detectors 21, 22 an output signal appears only when the respective threshold of the threshold value detector is exceeded. In all other cases an output signal appears at the output N of said threshold value detectors.

Furthermore, in both embodiments according to FIGS. 8 and 9 the threshold of the second threshold value detector 22 is higher than that of the first threshold value detector 21.

The 'N' output or the 'J' output of the threshold value detector 21 is connected in each case to display means 26 and 27 which in a manner still to be described are activated in the search operation or on determination of fabric at the end of the optical waveguide 8.

The output of the second threshold value detector denoted by 'J' is also connected to a display device 28 which additionally indicates that the end of the optical waveguide is adjacent to a material to be worked, for example the stone.

In the embodiment according to FIG. 8 the output of the threshold value switch 22 denoted by 'J' further actuates a switch 25 which may of course be an electronic switch. This switch connects the output signal of the signal amplifier 20 to the input of a curve shape discriminator 23 which determines the time function variation of the output signal of the detector arrangement 8. On closure of the switch 25 the curve shape discriminator 23 emits via the output line 20a a signal to the laser control circuit 24 which drives the laser 1 for emission of a working pulse. When the curve shape discriminator then detects the time function profile according to FIG. 7a or FIG. 5 typical of material to be worked it continuously controls the laser via the laser control circuit 24 in such a manner that said laser emits working pulses with a power sufficient for dielectric breakdown. The emission of working pulses of high power is continued until the curve shape discriminator detects the curve shape of FIG. 6 or 7b, whereupon via a second output line 23b the laser control is driven so that the power is immediately reduced, possibly also activating the optical switch 2 to interrupt immediately the further passage of the output pulse of laser to the optical wave guide so that the laser output pulse appearing at the end of the optical waveguide is shortened. When the optical switch is not used with shorter laser pulses the next laser pulse is reduced in its power density (measuring pulse). The output signal at the second output 23b of the curve shape discriminator is also used to reset the switch 25 to the open condition. Only laser pulses of lower power are then emitted and are used to search for further material to be worked, whereupon on detection of material to be worked in the manner described above the switch 25 is closed and the process is repeated.

The embodiment according to FIG. 9 is suitable in particular for a method in which alternately a measuring pulse of low power and a working pulse of higher power follow each other in each case, the working pulse however being triggered only when the preceding measuring pulse has detected material to be worked at the end of the optical wave guide 6.

For this purpose the output of the second threshold value switch 22 denoted by 'J' is connected to a first trigger circuit 40 which drives the laser control 24 in such a manner that the laser emits a working pulse.

If the output of the threshold value switch 22 designated by 'N' is activated only a weak measuring pulse is triggered via a second trigger circuit 41.

Of course, the first trigger circuit 40 can still be followed by a curve shape discriminator 23 in accordance with FIG. 8 which permits an evaluation of this curve shape.

Said curve shape discriminator may for example carry out a Fourier transformation and it could be formed by a fast analog/digital converter and a shift register including comparators. Further embodiments of such curve shape discriminators are well known to the expert.

At the end of the optical waveguide 6 adjacent the laser optical system or at another suitable point it is also possible to provide an acoustic detector which detects the acoustic signals accompanying the dielectric breakdown and prepares them for a further evaluation, not illustrated.

As a comparison of FIGS. 5 and 6, in the case illustrated in FIG. 5 where the laser pulse strikes a relatively hard material shortly after triggering of the laser pulse illustrated in the upper half of this Figure there is a rise of the output signal at the point A. In comparison, the rise of the output signal of the detector arrangement in accordance with FIG. 6 takes place much later when relatively soft material is struck; these two diagrams according to FIGS. 5 and 6 have been shown together in FIG. 10 for clarification. It is apparent from the diagram of FIG. 10 that when striking a stone the output signal of the detector arrangement rises after only about 100–150 nanoseconds whilst on striking tissue this rise does not take place until about 500 nanoseconds after triggering of the laser pulse. At this instant the laser pulse has not yet reached its full power so that via the line 11 and/or the line 12 with the aid of the fast optical switch 2 according to FIGS. 1 and 11 it is possible to terminate the laser pulse emerging at the end of the optical waveguide 6 before it reaches its maximum energy.

Figure 10:
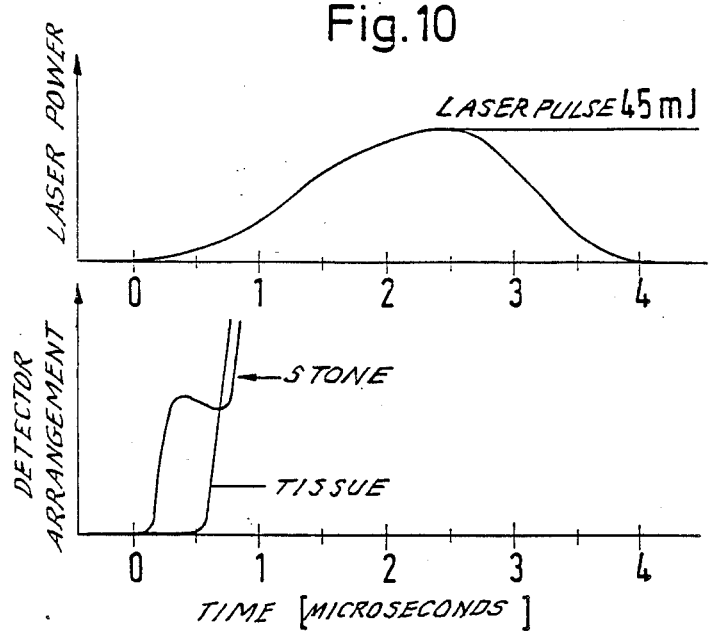
FIG. 10 shows a diagram to explain a further basic idea of the invention.
Figure 11:
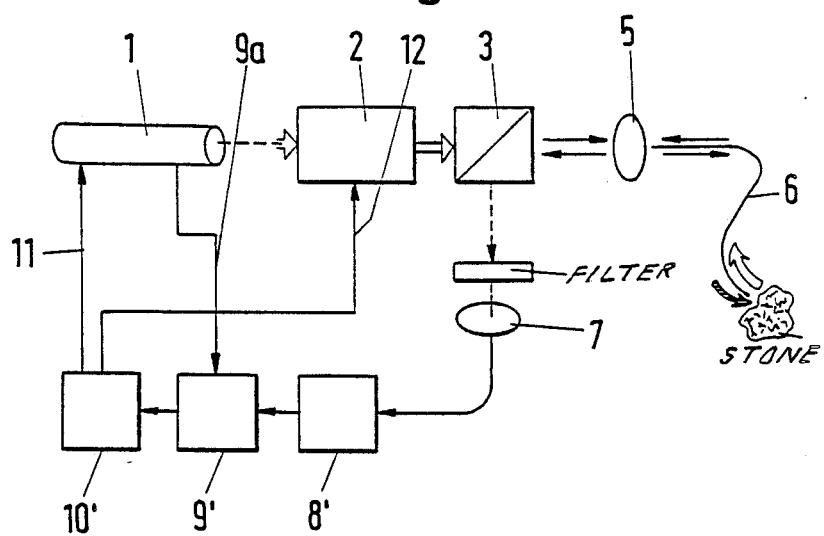
FIG. 11 shows an embodiment of the apparatus for the evaluation in accordance with the principles of FIG. 10.

The detection according to the invention of the conditions illustrated in FIG. 10 is possible with a relatively simple form of the evaluating circuit constructed as comparator 9' in accordance with FIG. 11 and containing for example a timing member which in the preceding case about 200 nanoseconds after the triggering of the laser pulse samples the output signal of the detector to determine whether the output signal of the detector has reached or exceeded a predetermined threshold value. If it has not the comparator 9' emits a control signal to the control circuit 10' which is disconnects the laser 1 and/or blocks the highspeed optical switch 2 so that the laser pulse entering the optical waveguide is terminated before reaching its maximum energy.

Thus, with simple construction the embodiment of the apparatus according to FIG. 11 provides a very effective and reliable disconnection of the laser pulse should the latter unintentionally strike material which is not to be worked.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. Method for material processing with the aid of a laser in which the laser light is directed via a laser optical system onto the material and the light reemitted or scattered back by the material is conducted via the laser optical system to a detector arrangement which is followed by an evaluating circuit for controlling the laser, wherein the amplitude-versus-time profile of the light incident on the detector arrangement is evaluated after passage of a predetermined period of time from the start of the laser light and is used for controlling the laser and/or an optical switch arranged in the output beam path of the laser.

2. Method according to claim 1, wherein until a desired relative position is reached between the laser optical system and the material to be processed the laser is operated with reduced power.

3. Method according to claim 2, wherein to find the desired relative position, the time function profile of the detector output signal is evaluated.

4. Method according to claim 1 wherein that after reaching the desired relative position between the laser optical system and the material to be processed a laser measuring pulse of lower power is first emitted and serves to check the nature and/or state of the material disposed in front of the laser optical system, and on detection of the correct material and/or material state subsequently a laser pulse of increased power is emitted for the material processing, whereupon a measuring pulse again follows.

5. Method according to claim 1, wherein the laser pulse supplied to the material to be processed is interrupted within a predetermined time after its triggering if by said time a predetermined measuring criterion of the output signal of the detector arrangement has not been detected.

6. Method according to claim 5, wherein the predetermined measuring criterion is an amplitude of the output signal of the detector arrangement lying above a threshold value.

7. Method according to claim 1 in which the material to be processed is uroliths or gall stones, embedded in body tissue, wherein the amplitude-versus-time profile of the light incident on the detector arrangement is measured and used to determine whether the laser optical system is directed onto the stone.

8. Method according to claim 7, wherein on emission of the measuring pulse with alignment onto the stone a higher scattering back than on direction onto the tissue embedding the stone occurs while on emission of the working pulse with alignment on the stone another time function of the light incident on the detector arrangement than with alignment on the tissue is detected, and these criteria are used for controlling the laser and/or the optical switch.

9. Method according to claim 8, wherein the laser pulse supplied to the material to be processed is terminated within a predetermined time after its triggering if the output signal of the detector arrangement within said time has not exceeded a predetermined threshold value.

10. Method according to claim 1, wherein in addition, the acoustic signal arising on dielectric breakdown is picked up and evaluated.

11. Apparatus for material processing with the aid of a laser which is followed by a laser optical system which directs laser pulses onto material to be processed and guides light reemitted or scattered back from said material onto a detector arrangement which is followed by an evaluating circuit for controlling the laser, wherein the evaluating circuit determines the amplitude-versus-time profile of the light incident on the detector arrangement after passage of a predetermined period of time from the start of a laser pulse, and the evaluating circuit in dependence upon the amplitude-versus-time profile of the light incident on the detector arrangement controls the laser and/or an optical switch interposed between the laser and the laser optical system.

12. Apparatus according to claim 11, wherein the laser optical system includes a semireflecting mirror which reflects to the detector arrangement light reemitted or scattered back by the material subjected to the laser pulse.

13. Apparatus according to claim 11, wherein the laser optical system includes a first optical waveguide which conducts the output pulses onto the material to be processed and a second optical waveguide which is substantially parallel to the first and which directs onto the detector arrangement the light reemitted back or scattered back by the material.

14. Apparatus according to claim 11 wherein the evaluating circuit includes first and second threshold detectors having inputs connected to the output of the detector arrangement, the threshold of the second threshold detector is greater than the threshold of the first threshold detector and the output active on exceeding the threshold of the second threshold value detector effects the control of the laser and/or of the optical switch.

15. Apparatus according to claim 14, wherein the output active on exceeding of the second threshold bracket of the second threshold value detector controls a switch means which connects the output of the detector arrangement to the input of a curve shape discriminator for analysing the time function of the output signal of the output arrangement, (8) and the curve shape discriminator in dependence upon the time function profile of the output signal of the detector arrangement drives a laser control circuit which controls the emission of a laser pulse with greater or smaller power and/or the permeability of the optical switch.

16. Apparatus according to claim 14, wherein the output active on exceeding of the threshold of the second threshold value detector is connected to the input of a first trigger circuit which effects via a laser control circuit the triggering of a working pulse while the output of the second threshold value switch representing non-exceeding of the threshold is connected to a second trigger circuit which via the laser control circuit effects the triggering of a measuring pulse.

17. Apparatus according to claim 11, wherein the evaluating circuit includes a comparator which furnishes an output signal when the output signal of the detector arrangement has not reached a threshold value within a predetermined time after triggering of a laser pulse.

18. Apparatus according to claim 17, wherein the output signal of the comparator controls the laser and/or an optical locking cell arranged in the beam path of the laser.

19. Apparatus according to claim 1, wherein the detector arrangement includes a plurality of detectors which respond to different spectral ranges of the light reemitted or scattered back or back by the material.

* * * * *